United States Patent
Nagare

(10) Patent No.: US 10,300,008 B2
(45) Date of Patent: May 28, 2019

(54) WATER-BASED COSMETIC

(71) Applicant: SHISEIDO COMPANY, LTD., Tokyo (JP)

(72) Inventor: Yuko Nagare, Kanagawa (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 15/321,811

(22) PCT Filed: Jun. 30, 2015

(86) PCT No.: PCT/JP2015/068776
§ 371 (c)(1),
(2) Date: Dec. 23, 2016

(87) PCT Pub. No.: WO2016/002752
PCT Pub. Date: Jan. 7, 2016

(65) Prior Publication Data
US 2017/0128352 A1 May 11, 2017

(30) Foreign Application Priority Data
Jun. 30, 2014 (JP) ................. 2014-133553

(51) Int. Cl.
A61K 8/894 (2006.01)
A61K 8/02 (2006.01)
A61K 8/04 (2006.01)
A61K 8/19 (2006.01)
A61K 8/26 (2006.01)
A61K 8/27 (2006.01)
A61K 8/29 (2006.01)
A61K 8/34 (2006.01)
A61K 8/36 (2006.01)
A61K 8/58 (2006.01)
A61K 8/73 (2006.01)
A61K 8/81 (2006.01)
A61K 8/87 (2006.01)
A61K 8/88 (2006.01)
A61K 8/891 (2006.01)
A61K 8/896 (2006.01)
A61Q 19/00 (2006.01)
A61Q 19/02 (2006.01)

(52) U.S. Cl.
CPC .............. A61K 8/894 (2013.01); A61K 8/022 (2013.01); A61K 8/04 (2013.01); A61K 8/19 (2013.01); A61K 8/26 (2013.01); A61K 8/27 (2013.01); A61K 8/29 (2013.01); A61K 8/34 (2013.01); A61K 8/361 (2013.01); A61K 8/585 (2013.01); A61K 8/73 (2013.01); A61K 8/731 (2013.01); A61K 8/8158 (2013.01); A61K 8/87 (2013.01); A61K 8/88 (2013.01); A61K 8/891 (2013.01); A61K 8/896 (2013.01); A61Q 19/00 (2013.01); A61Q 19/007 (2013.01); A61Q 19/02 (2013.01); A61K 2800/48 (2013.01); A61K 2800/596 (2013.01); A61K 2800/5922 (2013.01)

(58) Field of Classification Search
None
See application file for complete search history.

(56) References Cited

U.S. PATENT DOCUMENTS

| | | | |
|---|---|---|---|
| 2005/0228056 A1 | 10/2005 | Asai | |
| 2007/0071980 A1 | 3/2007 | Kamei | |
| 2012/0045403 A1* | 2/2012 | Ikebe | A61K 8/062 424/59 |
| 2013/0231401 A1 | 9/2013 | Hiruma et al. | |

FOREIGN PATENT DOCUMENTS

| | | |
|---|---|---|
| EP | 2 740 774 | 6/2014 |
| EP | 3 108 869 | 12/2016 |
| JP | 6-116120 | 4/1994 |
| JP | H06 116120 | 4/1994 |
| JP | 2009-234994 | 10/2009 |
| JP | 2009 234994 | 10/2009 |
| JP | 2010-254673 | 11/2010 |
| JP | 2011-236202 | 11/2011 |
| JP | 2011 236202 | 11/2011 |
| JP | 2012-111726 | 6/2012 |
| JP | 2012 111726 | 6/2012 |
| JP | 2012-162515 | 8/2012 |
| WO | WO 2004/006871 | 1/2004 |
| WO | WO 2012/053295 | 4/2012 |

OTHER PUBLICATIONS

Machine translation, JP H06-116120 (Year: 1994).*
PCT/JP2015/068776, International Search Report and Written Opinion, dated Oct. 6, 2015, 2 pages—English, 7 pages—Japanese.
EP 15815189.4, Communication pursuant to Rule 114(2) EPC dated Jan. 22, 2019, 5 pages—English.
EP 158151891.4, Extended European Search Report dated Jan. 22, 2018, 8 pages—English.

* cited by examiner

Primary Examiner — Bethany P Barham
Assistant Examiner — Barbara S Frazier
(74) Attorney, Agent, or Firm — Andrew F. Young, Esq.; Lackenbach Siegel, LLP

(57) ABSTRACT

The present invention relates to a water-based cosmetic wherein a hydrophobic powder is directly dispersed in the water phase of the water-based cosmetic, the water-based cosmetic having the excellent smoothness, water resistance and cosmetic durability characteristic of hydrophobic powders, while maintaining the refreshing sensation of use that is inherent in water-based cosmetics.
The invented water-based cosmetic is characterized by comprising: (A) 0.1 to 5 mass % of a polyether-modified silicone having an HLB (Si) of 5 to 14; (B) one or more hydrophilic thickeners; (C) a polyol and/or an ethyl alcohol; and (D) one or more hydrophobic powders chosen from among metal oxides hydrophobically treated without using a metal soap, hydrophobic organic powders and silicone powders; wherein the (D) hydrophobic powder is dispersed in the water phase.

5 Claims, No Drawings

WATER-BASED COSMETIC

CROSS REFERENCE TO RELATED APPLICATIONS

This application relates to and claims priority as a § 371 national phase, from PCT/JP2015/068776 filed Jun. 30, 2016, the entire contents of which are incorporated herein by reference, which in turn claims priority from JP 2014-133553 filed Jun. 30, 2014.

TECHNICAL FIELD

The present invention relates to a water-based cosmetic. More specifically, the invention relates to a water-based cosmetic wherein a hydrophobic powder is directly dispersed in the water phase of the water-based cosmetic, the water-based cosmetic having the excellent smoothness, water resistance and cosmetic durability characteristic of hydrophobic powders, while maintaining the refreshing sensation of use that is inherent in water-based cosmetics.

BACKGROUND ART

Oil-in-water type emulsified compositions are widely used as bases in skin-care preparations for external use, such as skin-care cosmetics or the like, that are applied directly to the skin, because they provide a fresh and refreshing sensation when applied to the skin. In particular, skin case and body care has come to include everyday protection of the skin from UV rays, and the importance of using oil-in-water type emulsified compositions as bases in such UV-care cosmetics is also increasing.

On the other hand, while metal oxide powders are known to have the function of UV scattering agents that protect the skin from UV rays, aside therefrom, they also have the functions of improving the texture during application, and concealing coloration and blotches, freckles and the like on the skin, so they have conventionally been widely added to various types of cosmetics. In recent years, metal oxides having hydrophobically treated surfaces have been used for the purposes of improving lack of squeakiness, water resistance, cosmetic durability and dispersibility.

When mixing a hydrophobically treated metal oxide powder such as hydrophobic fine-particle titanium oxide or hydrophobic fine-particle zinc oxide into an oil-in-water type emulsified composition, it is usually dispersed in a volatile oil using a low-HLB dispersing agent or special dispersing equipment such as a wet bead mill with strong pulverization energy, then emulsified. However, in order to mix a lot of powder in order to obtain sufficient UV ray protection ability, a large quantity of oil becomes necessary for dispersing the powder, as a result of which the texture can become oily and the freshness that is inherent in oil-in-water type emulsified compositions can be lost.

For example, Patent Document 1 describes an oil-in-water type emulsified sunscreen cosmetic wherein, in order to stably disperse a hydrophobically treated zinc oxide without using a special dispersion apparatus, a specific compound (octyltriethoxysilane or dimethylpolysiloxane) is used for the hydrophobic treatment of the zinc oxide, and this is dispersed in a specific oil (liquid higher fatty acid) using a specific dispersing agent (a carboxyl group-containing silicone or sugar ester). However, a large amount of volatile oil is required in order to stably disperse hydrophobically treated zinc oxide, as a result of which the total oil content increases and a refreshing texture is difficult to achieve.

Additionally, Patent Document 2 describes that, in order to stably blend hydrophobically treated powder particles into an oil-in-water type emulsified composition that uses an ionic water-soluble polymer compound as a thickener, hydrophobic powder particles are used as the powder particles, and furthermore, ion elution is prevented by mixing a specific polyether-modified silicone into the oil phase.

In this composition, the polyether-modified silicone acts as a gelling agent for gelling the oil phase which includes a silicone oil and hydrophobic powder particles, and prevents ion elution from the hydrophobic powder particles in the oil phase, thereby stabilizing the thickening due to the ionic polymers in the water phase. However, since the dispersion of powder in an oil phase is conventionally performed by mechanical force, a large amount of silicone oil must be added as a dispersion medium in order to sufficiently disperse the hydrophobic powder particles, and as with Patent Document 1, the total oil content increases and a refreshing texture is difficult to achieve. Furthermore, there are cases in which the hydrophobic powder particles absorb the oil in the oil phase, as a result of which the smooth sensation of use characteristic of hydrophobic powders is lost.

On the other hand, aside from the above-mentioned Patent Document 2, there have been other attempts to achieve stabilization of oil-in-water type emulsified compositions using polyether-modified silicones (Patent Documents 3 to 5). Patent Document 3 describes that a non-sticky, refreshing sensation of use, stability and a high SPF can be achieved by mixing a combination of polyether-modified silicone, a predetermined amount of an extender pigment, and a UV absorbing agent having absorption ability in the UV-A region. Patent Document 4 describes that excellent water resistance can be obtained after application to the skin, by forming an oil-in-water type emulsion using a polyether-modified silicone having an HLB (Si) of 5 to 10 as a surfactant, and further adding a predetermined amount of ethanol, a hydrophilic thickener and a polyol. Patent Document 5 describes that, by blending an aqueous dispersion of an oil-soluble UV absorbing agent into the water phase in a stable system similar to that of Patent Document 4, the UV protection effect was increased over the case of blending a UV absorbing agent into an oil phase.

However, none of Patent Documents 3 to 5 teaches a method of blending a high content of a hydrophobic metal oxide. On the contrary, Patent Document 3 describes that the emulsion stability becomes worse when adding hydrophobically treated talc as compared with the case where talc that has not been hydrophobically treated is added (Comparative Example 4), and Patent Document 5 describes that the texture is reduced when fine-particle titanium oxide is added (Comparative Example 2).

RELATED ART DOCUMENTS

Patent Documents

Patent Document 1: JP 2012-111726 A
Patent Document 2: WO 2004/006871
Patent Document 3: JP 2012-162515 A
Patent Document 4: JP 2010-254673 A
Patent Document 5: JP 2011-236202 A

SUMMARY OF THE INVENTION

Problems to be Solved by the Invention

The present invention was made in consideration of the above-mentioned drawbacks of the conventional art, and has the purpose of offering a water-based cosmetic that has the excellent smoothness, water resistance and cosmetic durability that are characteristic of hydrophobic powders, while maintaining the refreshing sensation of use that is inherently possessed by water-based cosmetics.

Means for Solving the Problems

As a result of repeating diligent research into solving the above-mentioned problems, the present inventors discovered that a water-based cosmetic containing a polyether-modified silicone having a specific HLB (Si), a hydrophilic thickener, and a polyol and/or an ethyl alcohol is capable of evenly and stably dispersing, in the water phase, a hydrophobic powder which would normally be blended in the oil phase, and as a result is capable of achieving excellent smoothness, water resistance and cosmetic durability while maintaining a refreshing texture, thereby bringing the present invention to completion.

In other words, the present invention is basically directed to a water-based cosmetic characterized by comprising:
(A) 0.1 to 5 mass % of a polyether-modified silicone having an HLB (Si) of 5 to 14;
(B) one or more hydrophilic thickeners;
(C) a polyol and/or an ethyl alcohol; and
(D) one or more hydrophobic powders chosen from among metal oxides hydrophobically treated without using a metal soap, hydrophobic organic powders and silicone powders; wherein the (D) hydrophobic powder is dispersed in the water phase.

Effects of the Invention

The water-based cosmetic according to the present invention, by using a combination of (A) a polyether-modified silicone with an HLB (Si) of 5 to 14 with (B) a hydrophilic thickener and (C) a polyol and/or an ethyl alcohol, allows (D) a hydrophobic powder to be uniformly and stably dispersed in the water phase of the water-based cosmetic. For this reason, there is no need to add large amounts of volatile oils or silicone oils which are conventionally added to disperse (D) hydrophobic powders, and a refreshing texture can be achieved. Additionally, by adding the hydrophobic powder not to the oil phase but to the water phase, a smooth sensation of use and excellent water resistance and cosmetic durability can be achieved.

MODES FOR CARRYING OUT THE INVENTION

The water-based cosmetic of the present invention comprises (A) a polyether-modified silicone having an HLB (Si) of 5 to 14; (B) a hydrophilic thickener; (C) a polyol and/or an ethyl alcohol; and (D) a specific hydrophobic powder as essential components.

Herebelow, the present invention will be described in detail.

For the purposes of the present invention, a water-based cosmetic refers to a cosmetic wherein at least 50 mass % of the cosmetic overall is composed of water, and includes (1) embodiments of cosmetics wherein the base consists only of aqueous components (cosmetics consisting essentially of aqueous components and powder components), and (2) embodiments of oil-in-water type emulsion cosmetics wherein the aqueous components form the external phase. In other words, "the powder is dispersed in the water phase", in the embodiments of (1) above, means that the powder is dispersed throughout the entire cosmetic, and in the embodiments of (2) above, means that the powder is dispersed in the external phase (water phase).

<(A) Polyether-Modified Silicone Having an HLB (Si) of 5 to 14>

The (A) polyether-modified silicone in the water-based cosmetic of the present invention is a silicone derivative having a polyoxyalkylene group chosen from among polyoxyethylenes (POE) and polyoxypropylenes (POP). In particular, the polyether-modified silicones represented by the following general formula are preferred.
[Chemical Formula 1]

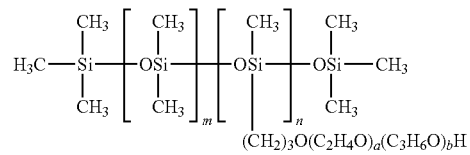

In the above formula, m is 1 to 1000, preferably 5 to 500, and n is 1 to 40. Additionally, m:n is preferably 200 : 1 to 1 : 1. Additionally, a is 5 to 50 and b is 0 to 50.

The molecular weight of the polyether-modified silicone is not particularly limited, but should preferably be in the range of 3,000 to 60,000, and more preferably 3,000 to 40,000. A particularly excellent texture can be achieved by using a low molecular weight polyether-modified silicone.

The polyether-modified silicone used in the present invention is chosen from those having an HLB (Si) of 5 to 14, more preferably 7 to 14. The HLB (Si) mentioned here is a value determined by the following computational formula:

$$\frac{\text{Molecular weight of polyoxyethylene } (POE) \text{ and polyoxypropylene} (POP)}{\text{Molecular weight}} \times 20 \qquad \text{[Equation 1]}$$

As the (A) polyether-modified silicone, one or more types chosen from those that are conventionally used in cosmetics and the like may be used. Specific examples include PEG/PPG-19/19 dimethicone, PEG/PPG-30/10 dimethicone, PEG-12 dimethicone and PEG-1 1 methyl ether dimethicone.

The (A) polyether-modified silicone used in the present invention may be one that is commercially available, for example:
Product name BY11-030 (manufactured by Toray Dow Corning: PEG/PPG-19/19 dimethicone, HLB (Si)=7.7)
Product name SH3773M (manufactured by Toray Dow Corning: PEG-12 dimethicone, HLB (Si)=7.7)
Product name BY25-339 (manufactured by Toray Dow Corning: PEG/PPG-30/10 dimethicone, HLB (Si) =12.2)
Product name KF6011 (manufactured by Shin-etsu Chemical: PEG-11 methyl ether dimethicone, HLB (Si)=12.7)

The blended amount of the (A) polyether-modified silicone should preferably be at least 0.1 mass %, at least 0.2 mass %, at least 0.3 mass %, at least 0.4 mass % or at least 0.5 mass %, and at most 5 mass %, at most 4 mass % or at most 3 mass % with respect to the total amount of the water-based cosmetic of the present invention. The specific range of the blended amount should be 0.1 to 5 mass %, preferably 0.5 to 5 mass %, and more preferably 0.5 to 3 mass %. If the blended amount is less than 0.1 mass %, there may be cases in which a stable composition in which the (D) hydrophobic powder is uniformly dispersed cannot be obtained, and if more than 5 mass % is blended, the texture may be sticky.

<(B) Hydrophilic Thickener>

The (B) hydrophilic thickener in the water-based cosmetic of the present invention is not particularly limited as long as it is one that is normally used in cosmetic products. Examples include natural or semi-synthetic water-soluble polymers, synthetic water-soluble polymers and inorganic water-soluble polymers.

As the natural or semi-synthetic water-soluble polymers, polysaccharides and derivatives thereof (including water-soluble alkyl-substituted polysaccharide derivatives) are preferably used. Specific examples include plant-based polymers such as gum arabic, tragacanth gum, galaetan, guar gum, carob gum, karaya gum, carrageenan, pectin, agar, quince seed (marmelo), algecolloid (phaeophyceae extract), starch (rice, corn, potato, wheat) and glycyrrhizinic acid; microbe-based polymers such as xanthan gum, dextran, succinoglycan and pullulan; starch-based polymers such as carboxymethyl starch and methylhydroxypropyl starch; cellulose-based polymers such as methyl cellulose, nitrocellulose, ethyl cellulose, methyl hydroxypropyl cellulose, hydroxyethyl cellulose, sodium cellulose sulfate, hydroxypropyl cellulose, sodium carboxymethyl cellulose (CMC), crystalline cellulose and cellulose powder; and alginic acid-based polymers such as sodium alginate and propylene glycol esters of alginic acid.

The synthetic water-soluble polymers include ionic or non-ionic water-soluble polymers, for example, vinyl-based polymers such as polyvinyl alcohol, polyvinyl methyl ether, polyvinyl pyrrolidone and carboxyvinyl polymers (carbomers); polyoxyethylene-based polymers such as polyethylene glycol (molecular weight 1500, 4000, 6000); copolymer-based polymers such as polyoxyethylene/polyoxypropylene copolymers; acryl-based polymers such as sodium polyacrylate, poly ethyl acrylate, polyacrylamide compounds and acrylic acid/alkyl methacrylate copolymers (product name "pemulen TR-1"); and polyethylene imine and cationic polymers.

The polyacrylamide compounds particularly include polyacrylamide compounds consisting of homopolymers, copolymers or crosspolymers containing one or more constituent units chosen from among 2-acrylamido-2-methylpropane sulfonic acid (hereinafter sometimes abbreviated to "AMPS"), acrylic acid and derivatives thereof.

Specific examples of such polyacrylamide compounds include vinylpyrrolidone/2-acrylamido-2-methylpropane sulfonic acid (salt) copolymers, dimethylacrylarnide/2-acrylamido-2-methylpropane sulfonic acid (salt) copolymers, acrylamide/2-acrylamiclo-2-methylpropane sulfonic acid copolymers, dimethylacrylainide/2-acrylamido-2-methylpropane sulfonic acid crosspolymers crosslinked with methylenebisacrylamide, mixtures of polyacrylamide and sodium polyacrylate, sodium acrylate/2-acrylamido-2-methylpropane sulfonic acid copolymers, hydroxyethyl acrylate/2-acrylamido-2-methylpropane sulfonic acid (salt) copolymers, ammonium polyacrylate, polyacrylamide/ammonium acrylate copolymers, and acrylamide/sodium acrylate copolymers. However, the compounds are not limited to these examples.

Preferred examples of salts in the previous paragraph include alkali metal salts (such as calcium salts and magnesium salts), ammonium salts, organic amine salts (such as monoethanolamine salts, diethanolamine salts, and triethanolamine salts). One or more of these polyacrylamide compounds may be used.

These polyacrylamide compounds may be synthesized or obtained as commercial products. For example, the vinyl pyrrolidone/2-acrylarnido-2-methylpropane sulfonic acid (salt) copolymer may be "Aristoflex AVC" (manufactured by Clariant), the sodium alylate/2-acrylamido-2-methylpropane sulfonic acid (salt) copolymer may be "Simulgel EG" (manufactured by Sepic) or "Simulgel EPG" (manufactured by Sepic), the acrylamide/2-acrylamido-2-methylpropane sulfonic acid sodium salt copolymer may be "Simulgel 600" (manufactured by Sepic), the acrylamide/2-acrylamido-2-methylpropane sulfonic acid (salt) may be "Sepigel 305" (manufactured by Sepic) or "Sepigel 501" (manufactured by Sepic), the homopolymer of a 2-acrylamido-2-methylpropane sulfonic acid sodium salt may be "1-lostacerin AMPS" (manufactured by Clariant) or "Simulgel 800" (manufactured by Sepic), and the dimethylacrylamide/2-acrylamido-2-methylpropane sulfonic acid may be "SU-Polymer 0-1" (manufactured by Toho Chemical Industry).

In the present invention, a crosspolymer of dimethylacrylarnide and an acryloyl dimethyl taurine salt is particularly preferred, a specific example being a (dimethylacrylarnide/sodium acryloyl dimethyl taurate) crosspolymer.

Examples of inorganic water-soluble polymers include bentonite, Al—Mg silicate (product name "Veegum"), laponite, hectorite and silicic anhydride.

The (B) hydrophilic thickener in the water-based cosmetic of the present invention may be a combination of one or more types. In particular, it is preferable to include at least one type chosen from among polysaccharides such as succinoglycan, xanthan gum and carboxymethylcellulose, derivatives thereof, and polyacrylamide compounds.

The blended amount of the (B) hydrophilic thickener in the water-based cosmetic of the present invention should preferably be at least 0.01 mass %, at least 0.03 mass %, at least 0.05 mass/0, at least 0.08 mass % or at least 0.1 mass %, and at most 3 mass %, at most 2.5 mass %, at most 2 mass % or at most 1 mass % with respect to the total amount of the cosmetic. The specific range of the blended amount should be 0.01 to 3 mass %, preferably 0.05 to 2 mass %, and more preferably 0.1 to I mass %. If the blended amount is less than 0.01 mass %, there may be cases in which a stable composition in which the hydrophobic powder is uniformly dispersed cannot be obtained, and if more than 3 mass % is blended, there may be a heavy texture at the time of application.

<(C) Polyol and/or Ethyl Alcohol>

The water-based cosmetic of the present invention further contains a (C) polyol and/or ethyl alcohol as an essential component.

The polyol used in the present invention is not particularly limited as long as it is one that is normally used in cosmetic products, and examples include glycerin, 1,3-butylene glycol, dipropylene glycol and propylene glycol.

The blended amount of the (C) polyol and/or ethyl alcohol in the water-based cosmetic of the present invention is at least ½ the blended amount of the (D) hydrophobic powder, and preferable at least 1 time, at least 1.5 times, at least 2 times, at least 2.5 times, or at least 3 times the amount, When considering the range of the blended amount of the (D) hydrophobic powder, it should be at least 0.25 mass %, at least 0.5 mass %, at least 1 mass %, at least 1.25 mass % or at least 1.5 mass % with respect to the total amount of the water-based cosmetic. If the blended amount is too small, a stable cosmetic may not be obtained. Additionally, if the blended amount is too much, there may be a heavy texture at the time of application, so typically, the upper limit of the blended amount should be at most 40 mass %, at most 30 mass %, or at most 20 mass % with respect to the total amount of the water-based cosmetic of the present invention. Specific ranges of the blended amount are 0.25 to 40 mass %, 1 to 30 mass % and 1.5 to 20 mass %.

<(D) Hydrophobic Powder>

The (D) hydrophobic powder blended into the water-based cosmetic of the present invention is of one or more types chosen from among (D1) metal oxides hydrophobically treated without using a metal soap, (D2) hydrophobic organic powders and (D3) silicone powders.

The (D1) metal oxides hydrophobically treated without using a metal soap (hereinafter sometimes referred to simply as "hydrophobically treated metal oxide") are powder particles having a metal oxide powder particle as the base material, the surface of which is subjected to a hydrophobic treatment.

Examples of the base materials for the hydrophobically treated metal oxide include titanium oxide, iron oxide, magnesium oxide, zinc oxide, calcium oxide and aluminum oxide. Additionally, a composite powder particle composed of a plurality of base materials may also be used.

The hydrophobic treatment to be performed on the base material powder particles may include various surface treatments that can be used as a surface treatment for powders blended into cosmetics and the like. For example, a fluorine compound treatment, a silicone treatment, a silane coupler treatment, a titanium coupler treatment, an oil treatment, an N-acylated lysine treatment, a polyacrylic acid treatment, an amino acid treatment, an inorganic compound treatment, a plasma treatment, a mechanochemical treatment, a silane compound or a silazane compound may be used. However, there may be cases in which the desired dispersibility is not obtained when the hydrophobic treatment is performed using a metal soap such as aluminum stearate. Therefore, the (D1) hydrophobically treated metal oxide in the present invention refers to a "metal oxide hydrophobically treated without using a metal soap".

Particularly preferred as a hydrophobic treatment for a metal oxide powder in the present invention is a silicone treatment or a fatty acid dextrin treatment.

Examples of silicone treatments include treatments using silicone oils such as methylhydrogen polysiloxane, dimethylpolysiloxane (dimethicone) and methylphenylpolysiloxane; alkylsilanes such as methyltriethoxysilane, ethyltriethoxysilane, hexyltriethoxysilane and octyltriethoxysilane; and fluoroalkylsilanes such as trifluoromethylethyl trimethoxysilane and heptadecafluorodecyl trimethoxysilane.

An example of a fatty acid dextrin treatment is a treatment by dextrin palmitate or the like. Such hydrophobic treatments can be performed in accordance with conventional methods, and one or a combination of two or more hydrophobic treatment agents may be used.

The (D1) hydrophobically treated metal oxide used in the present invention may be one that is commercially available, examples of which include Finex-50W-122, STR-100C-LP (manufactured by Sakai Chemical Industry), MPY-1133M, MZX-3040TS and MTY-110M3S (manufactured by Tayca).

As the (D2) hydrophobic organic powder, a polyamide resin powder (nylon powder), a polyethylene powder, a polyester powder, a polyurethane powder, a polymethyl methacrylate powder, a polystyrene powder, a copolymer resin powder of styrene and acrylic acid, a benzoguanamine resin powder, an polytetrafluoro ethylene powder, or a hydrophobically treated cellulose powder or starch powder may be used. Among these, those chosen from the group consisting of polymethyl methacrylate powder, nylon powder, polyurethane powder, polyethylene powder and polystyrene powder are preferable.

Examples of commercially available (D2) hydrophobic organic powders include Matsumoto Microsphere M-330 (manufactured by Matsumoto Yushi-Seiyaku), Plastic Powder D-400 and Plastic Powder D-800 (manufactured by Toshiki Pigment).

Specific examples of the (D3) silicone powder include silicone resin powders such as dimethicone/vinyl dimethicone crosspolymers, dimethicone/phenyl dimethicone crosspolymers, polyorganosilsesquioxane, and vinyl dimethicone/methicone silsesquioxane crosspolymers. Examples of commercially available products include Tospearl 2000B (manufactured by Momentive Performance Materials), Trefil E-506 (manufactured by Toray Dow Corning) and KSP-101 (manufactured by Shin-etsu Chemical).

The size and shape of the (D) hydrophobic powder in the present invention are not particularly limited, and for example, shapes such as spherical, plate-shaped, petal-shaped, flake-shape, rod-shaped, spindle-shaped, needle-shaped and irregularly shaped are possible. As the size of the (D) hydrophobic powder, one having an average particle size of about 2 nm to 5 μm by spherical particle conversion is preferably used. If a spherical powder shape is used, the texture is excellent, while a wrinkle concealing effect and a rough skin improving effect making use of the reflection of light can be provided. The (D1) hydrophobically treated metal oxide can also function as a UV scattering agent, and fine-particle (average particle size=about 1 μm or less) titanium oxide or zinc oxide is preferable.

The blended amount of the (D) hydrophobic powder in the water-based cosmetic of the present invention should preferably be at least 0.5 mass %, at least 1 mass %, at least 2 mass %, at least 3 mass %, at least 4 mass % or at least 5 mass %, and at most 35 mass %, at most 30 mass %, at most 25 mass % or at most 20 mass % with respect to the total amount of the water-based cosmetic of the present invention. The specific range of the blended amount should be 0.5 to 35 mass %, preferably 3 to 25 mass %, and more preferably 5 to 20 mass %. If the blended amount is less than 0.5 mass %, the effect of including the powder is not adequately achieved, and if the blended amount is more than 30 mass %, there is a tendency for problems in texture to occur, such as squeakiness, unevenness and stickiness.

In addition to the aforementioned components, the water-based cosmetic of the present invention may contain other optional components that can be blended into a water-based cosmetic, within a range not interfering with the effects of the present invention. Examples of other optional components, while not limiting, include thickeners other than those mentioned above, humectants, oils, UV absorbers, pH adjusters, neutralizing agents, antioxidants, preservatives, chelating agents, emollients, plant extracts, fragrances, pigments and various medicinal agents.

When the base materials constituting the water-based cosmetic are only in the form of aqueous components, the water-based cosmetic of the present invention can be made by preparing a powder portion by stirring and mixing the (A) polyether-modified silicone, (C) polyol and/or ethyl alcohol and (D) hydrophobic powder, and adding this mixture to a water phase portion (base) containing the (B) hydrophilic thickener.

Additionally, when the water-based cosmetic is in the form of an oil-in-water type emulsified composition, it can be made by separately preparing an oil phase portion and a water phase portion containing the (B) hydrophilic thickener, adding the oil phase portion to the water phase portion and emulsifying to prepare an oil-in-water type emulsified composition (base), while on the other hand preparing a powder portion by stirring and mixing the (A) polyether-modified silicone, (C) polyol and/or ethyl alcohol and (D) hydrophobic powder, and mixing this into the aforementioned emulsion (base).

The water-based cosmetic of the present invention is capable of stably dispersing the (D) hydrophobic powder in the water phase, and is therefore capable of providing the excellent smoothness, water resistance and cosmetic durability possessed by (D) hydrophobic powders while maintaining the freshness that is inherent in water-based cosmetics. Additionally, when a (D) hydrophobic powder that has a wrinkle concealing effect or a rough skin improving effect is added, a skin texture improving effect can also be expected. Additionally, when a powder (UV scattering agent) that has UV protection ability such as hydrophobic fine-particle titanium oxide or hydrophobic fine-particle zinc oxide is used as the (D) hydrophobic powder, a sunscreen cosmetic with a good texture can be obtained. In water-based cosmetics in the form of oil-in-water type emulsions, when a UV scattering agent is blended as the hydrophobic powder and a UV absorbing agent is blended in the oil phase, the UV absorbing agent and the UV scattering agent will act cooperatively to synergistically improve the UV protection effect. However, in order to maintain the fresh sensation of use, the blended amount of the oil phase component including the UV absorbing agent should preferably be at most 20 mass %, at most 15 mass %, at most 10 mass %, at most 8 mass %, at most 5 mass % or at most 3 mass %. Since the water-based cosmetic of the present invention has a UV scattering agent uniformly dispersed in the water phase, sufficient UV protection ability can be obtained even if the blended amount of oil-soluble UV scattering agent is small.

EXAMPLES

Herebelow, the present invention will be explained in further detail by providing specific examples, but the present invention is not limited to the following examples. Additionally, the blended amounts in the following examples are indicated in mass % where not especially mentioned to be otherwise.

Examples 1 to 4 and Comparative Examples 1 to 3

A water phase portion and a powder portion having the compositions shown in the below-indicated Table 1 were separately stirred and mixed until they were uniform, and the powder portion was added to the water phase portion to prepare a water-based cosmetic. The resulting cosmetics were observed by their external appearance and by using an optical microscope (400×), to evaluate the dispersion stability of the powder according to the following criteria.

<Evaluation Criteria>
A: The hydrophobic powder was uniformly dispersed in the oil
B: The hydrophobic powder was uniformly dispersed by external appearance, but slight aggregation was observed when studied under an optical microscope
C: Some aggregation of the hydrophobic powder was observed by external appearance
D: Most of the hydrophobic powder was aggregated

TABLE 1

| | | Ex. 1 | Ex. 2 | Ex. 3 | Ex. 4 | Comp. Ex. 1 | Comp. Ex. 2 | Comp. Ex. 3 |
|---|---|---|---|---|---|---|---|---|
| Water Phase Portion | Ion exchange water | bal | bal | bal | bal | bal | bal | bal |
| | Glycerin | 5 | 5 | 5 | 5 | 5 | 5 | 5 |
| | Succinoglycan | 0.2 | 0.2 | 0.2 | 0.2 | 0.2 | 0.2 | 0.2 |
| | Buffer | s.a. | s.a. | s.a. | s.a. | s.a. | s.a. | s.a. |
| | Phenoxyethanol | 0.5 | 0.5 | 0.5 | 0.5 | 0.5 | 0.5 | 0.5 |
| Powder Portion | 1,3-butylene glycol | 10 | 10 | 10 | 10 | 10 | 10 | 10 |
| | PEG/PPG-19/19 dimethicone (HLB (Si) = 7.7) *1 | 0.5 | — | — | — | — | — | — |
| | Decamethyl pentasiloxane *1 | 0.5 | — | — | — | — | — | — |
| | PEG/PPG-30/10 dimethicone (HLB (Si) = 12.2) *2 | — | 0.5 | — | — | — | — | — |
| | Dipropylene glycol *2 | — | 0.5 | — | — | — | — | — |
| | PEG-12 dimethicone (HLB (Si) = 7.7) *3 | — | — | 0.5 | — | — | — | — |
| | PEG-11 methyl ether dimethicone (HLB (Si) = 12.7) *4 | — | — | — | 0.5 | — | — | — |
| | PEG-10 dimethicone (HLB (Si) = 4.5) *5 | — | — | — | — | 0.5 | — | — |
| | Polyoxyethylene-60 hydrogenated castor oil (HLB = 14) | — | — | — | — | — | 0.5 | — |
| | Polymethyl silsesquioxane powder | 5 | 5 | 5 | 5 | 5 | 5 | 5 |

TABLE 1-continued

|  |  | Ex. 1 | Ex. 2 | Ex. 3 | Ex. 4 | Comp. Ex. 1 | Comp. Ex. 2 | Comp. Ex. 3 |
|---|---|---|---|---|---|---|---|---|
| Eval. | Dispersibility of hydrophobic powder in water phase | A | A | A | A | D | C | D |

*[1] Product name: BY11-030 (manufactured by Toray Dow Corning)
*[2] Product name: BY25-339 (manufactured by Toray Dow Corning)
*[3] Product name: SH3773M (manufactured by Toray Dow Corning)
*[4] Product name: KF6011 (manufactured by Shin-etsu Chemical)
*[5] Product name: KF6017 (manufactured by Shin-etsu Chemical)

As demonstrated in Examples 1 to 4, while the dispersion of the hydrophobic powder in the water phase was possible when using the polyether-modified silicones having an HLB (Si) in the range of 5 to 14, the hydrophobic powder was not able to be dispersed in Comparative Example 1 wherein the HLB (Si) was less than S. Additionally, when the polyether-modified silicone was replaced with a hydrocarbon-based surfactant, good dispersion was not possible even when the surfactant had a high HLB (HLB=14) (Comparative Example 2). Furthermore, the hydrophobic powder was also not able to be dispersed when neither a polyether-modified silicone nor a surfactant was used (Comparative Example 3).

Examples 5 to 13 and Comparative Example 4

The water-based cosmetics having the compositions shown in the following Table 2 and Table 3 were prepared by the same method as in Example 1 above, and the dispersion stabilities of the cosmetics were evaluated in accordance with the above-described criteria. The results are shown together in Table 2 and Table 3.

TABLE 2

|  |  | Ex. 5 | Ex. 6 | Ex. 7 | Comp. Ex. 4 | Ex. 8 |
|---|---|---|---|---|---|---|
| Water Phase Portion | Ion exchange water | bal | bal | bal | bal | bal |
|  | Glycerin | 5 | 5 | 5 | 5 | 5 |
|  | Carboxymethyl cellulose | 0.1 | 0.1 | 0.1 | 0.1 | 0.1 |
|  | Succinoglycan | 0.1 | 0.1 | 0.1 | 0.1 | 0.1 |
|  | (Dimethylacrylamide/ sodium acryloyl dimethyl taurate) crosspolymer | 0.2 | 0.2 | 0.2 | 0.2 | 0.2 |
|  | Chelating agent | s.a. | s.a. | s.a. | s.a. | s.a. |
|  | Buffer | s.a. | s.a. | s.a. | s.a. | s.a. |
|  | Phenoxyethanol | 0.5 | 0.5 | 0.5 | 0.5 | 0.5 |
| Powder Portion | Ethyl alcohol | 10 | 10 | 10 | 10 | 10 |
|  | PEG-11 methyl ether dimethicone (HLB (Si) = 12.7) *[4] | 0.5 | 0.5 | 0.5 | 0.5 | 0.5 |
|  | Dimethicone/hydrogendimethicone-treated silica-coated fine-particle zinc oxide | 5 | — | — | — | — |
|  | Tetrahydrotetramethyl-cyclotetrasiloxane-treated iron oxide | 0.02 | — | — | — | — |
|  | Octyltriethoxysilane-treated titanium oxide | — | 5 | — | — | — |
|  | Dextrin palmitate-treated fine-particle zinc oxide | — | — | 5 | — | — |
|  | Stearic acid, aluminum hydroxide-treated fine-particle titanium oxide | — | — | — | 5 | — |
|  | (Dimethicone/vinyl dimethicone/methicone) crosspolymer | — | — | — | — | 5 |
|  | Spherical polymethyl methacrylate powder | — | — | — | — | — |
|  | Spherical nylon powder | — | — | — | — | — |
|  | Urethane resin powder | — | — | — | — | — |
|  | Spherical polyethylene powder | — | — | — | — | — |
|  | (Diphenyl dimethicone/vinyl diphenyl dimethicone/silsesquioxane) crosspolymer | — | — | — | — | — |
| Eval. | Dispersibility of hydrophobic powder in water phase | A | A | B | D | A |

*[4] Product name: KF6011 (manufactured by Shin-etsu Chemical)

TABLE 3

|  |  | Ex. 9 | Ex. 10 | Ex. 11 | Ex. 12 | Ex. 13 |
|---|---|---|---|---|---|---|
| Water Phase Portion | Ion exchange water | bal | bal | bal | bal | bal |
|  | Glycerin | 5 | 5 | 5 | 5 | 5 |
|  | Carboxymethyl cellulose | 0.1 | 0.1 | 0.1 | 0.1 | 0.1 |
|  | Succinoglycan | 0.1 | 0.1 | 0.1 | 0.1 | 0.1 |
|  | (Dimethylacrylamide/ sodium acryloyl dimethyl taurate) crosspolymer | 0.2 | 0.2 | 0.2 | 0.2 | 0.2 |
|  | Chelating agent | s.a. | s.a. | s.a. | s.a. | s.a. |
|  | Buffer | s.a. | s.a. | s.a. | s.a. | s.a. |
|  | Phenoxyethanol | 0.5 | 0.5 | 0.5 | 0.5 | 0.5 |
| Powder Portion | Ethyl alcohol | 10 | 10 | 10 | 10 | 10 |
|  | PEG-11 methyl ether dimethicone (HLB (Si) = 12.7) *[4] | 0.5 | 0.5 | 0.5 | 0.5 | 0.5 |
|  | Dimethicone/hydrogendimethicone-treated silica-coated fine-particle zinc oxide | — | — | — | — | — |
|  | Tetrahydrotetramethyl-cyclotetrasiloxane-treated iron oxide | — | — | — | — | — |
|  | Octyltriethoxysilane-treated titanium oxide | — | — | — | — | — |
|  | Dextrin palmitate-treated fine-particle zinc oxide | — | — | — | — | — |
|  | Stearic acid, aluminum hydroxide-treated fine-particle titanium oxide | — | — | — | — | — |
|  | (Dimethicone/vinyl dimethicone/methicone) crosspolymer | — | — | — | — | — |
|  | Spherical polymethyl methacrylate powder | 5 | — | — | — | — |
|  | Spherical nylon powder | — | 5 | — | — | — |
|  | Urethane resin powder | — | — | 5 | — | — |

TABLE 3-continued

|  | | Ex. 9 | Ex. 10 | Ex. 11 | Ex. 12 | Ex. 13 |
|---|---|---|---|---|---|---|
| | Spherical polyethylene powder | — | — | — | 5 | — |
| | (Diphenyl dimethicone/vinyl diphenyl dimethicone/silsesquioxane) crosspolymer | — | — | — | — | 5 |
| Eval. | Dispersibility of hydrophobic powder in water phase | A | A | A | A | A |

*[4] Product name: KF6011 (manufactured by Shin-etsu Chemical)

As demonstrated in Examples 5 to 7, the hydrophobic powders consisting of metal oxides with surfaces hydrophobically treated without using a metal soap were dispersed well in the water phase in the systems of the present invention. In particular, excellent dispersibility was exhibited when using a silicone-treated metal oxide powder. However, as shown in Comparative Example 4, those that were treated with a metal soap (aluminum stearate) were not able to be well dispersed. Additionally, as shown in Examples 8 to 13, when a hydrophobic organic powder and a silicone powder were used, uniform dispersion was achieved in all cases.

Example 14 and Comparative Example 5

The water phase portions and oil phase portions shown in Table 4 below were each heated to 70° C. and fully melted. The oil phase portion was added to the water phase portion, emulsified with an emulsifier, and cooled. At this time, the powder portion was mixed into the water phase before emulsification in Comparative Example 5, but in Example 14, the stirred and mixed powder portion was mixed into the oil-in-water type emulsified composition after cooling.

The resulting compositions were used as cosmetic bases, and the freshness, smoothness, lightness of spread, and cosmetic durability at that time were evaluated by 10 expert evaluation panelists using the following criteria.
<Evaluation Criteria>
A: Evaluated as excellent by 8 to 10 panelists
B: Evaluated as excellent by 5 to 7 panelists
C: Evaluated as excellent by 4 or fewer panelists

TABLE 4

| | | Ex. 14 | Comp. Ex. 5 |
|---|---|---|---|
| Water Phase Portion | Ion exchange water | bal | bal |
| | Ethyl alcohol | — | 5 |
| | Dipropylene glycol | — | 8 |
| | Glycerin | 6 | 6 |
| | Bentonite | 0.5 | 0.5 |
| | Xanthan gum | 0.2 | 0.2 |
| | Buffer | s.a. | s.a. |
| | Potassium hydroxide | s.a. | s.a. |
| | Preservative | s.a. | s.a. |
| Oil Phase Portion | Glyceryl stearate | 2 | 2 |
| | Stearic acid | 0.5 | 0.5 |
| | Behenic acid | 0.3 | 0.3 |
| | Isostearic acid | 0.5 | 0.5 |
| | Cetyl 2-ethylhexanoate | 5 | 5 |
| | Ethylhexyl methoxycinnamate | 5 | 5 |
| Powder Portion | Ethyl alcohol | 5 | — |
| | Dipropylene glycol | 8 | — |
| | PEG-12 dimethicone (HLB (Si) = 7.7) *[3] | 1 | — |
| | Octyltriethoxysilane-treated titanium oxide | 3 | — |
| | Dimethicone/hydrogendimethicone-treated silica-coated zinc oxide | 5 | — |
| | (Dimethicone/vinyl dimethicone/methicone) crosspolymer | 2 | — |
| | Pigment-grade titanium oxide | — | 3 |
| | Fine-particle zinc oxide | — | 5 |
| | Spherical silica | — | 2 |
| Eval. | Freshness | A | A |
| | Smoothness | A | B |
| | Lightness of spread | A | C |
| | Cosmetic durability | A | C |

*[3] Product name: SH3773M (manufactured by Toray Dow Corning)

As demonstrated in Example 14, a cosmetic base in accordance with the present invention having a silicone-treated metal oxide and a silicone powder dispersed in the water phase exhibited the smoothness, lightness of spread and cosmetic durability that are characteristic of hydrophobic powders, while retaining the freshness of an oil-in-water type emulsified composition. On the other hand, as shown in Comparative Example 5, when a hydrophilic powder was blended instead of a hydrophobic powder, the smoothness, lightness of spread and cosmetic durability were found to be insufficient.

Herebelow, formulation examples of the water-based cosmetic of the present invention will be provided. The present invention is not in any way limited by these formulation examples, and needless to say, they fall within the scope of the claims. The blended amounts are all indicated in mass % with respect to the water-based cosmetic.

Formulation Example 1

Whitening Lotion

| (Component) | Blended amount (%) |
|---|---|
| Ion exchange water | bal |
| Glycerin | 5.0 |
| Dipropylene glycol | 2.0 |
| 1,3-butylene glycol | 5.0 |
| Carboxyvinyl polymer | 0.2 |
| Xanthan gum | 0.05 |
| Tranexamic acid | 2.0 |
| Potassium salt of 4-methoxysalicylic acid | 1.0 |
| Dipotassium glycyrrhizinate | 0.1 |
| Tocopherol acetate | 0.1 |
| PEG-11 methylether dimethicone *[4] | 1.0 |
| Spherical polymethyl silsesquioxane powder | 5.0 |
| Triethanolamine | s.a. |
| Antioxidant | s.a. |
| Preservative | s.a. |

Formulation Example 2

Lotion

| (Component) | Blended amount (%) |
|---|---|
| Ion exchange water | bal |
| Ethyl alcohol | 5.0 |
| Glycerin | 3.0 |
| 1,3-butylene glycol | 5.0 |

-continued

| (Component) | Blended amount (%) |
|---|---|
| (Dimethylacylamide/sodium acryloyl dimethyl taurate) crosspolymer | 0.4 |
| Succinoglycan | 0.1 |
| PEG-12 dimethicone *³ | 1.0 |
| Octyltriethoxysilane-treated titanium oxide | 4.0 |
| Spherical polymethyl methacrylate powder | 1.0 |
| Chelating agent | s.a. |
| Buffer | s.a. |
| Preservative | s.a. |
| Fragrance | s.a. |

Formulation Example 3

Milky Lotion

| (Component) | Blended amount (%) |
|---|---|
| Ion exchange water | bal |
| Ethyl alcohol | 3.0 |
| (Sodium acrylate/sodium acryloyl dimethyl taurate) copolymer | 0.4 |
| Carboxymethyl cellulose | 0.05 |
| Glycerin | 5.0 |
| Erythritol | 2.0 |
| Dipropylene glycol | 7.0 |
| Behenyl alcohol | 1.0 |
| Batyl alcohol | 0.5 |
| Squalane | 6.0 |
| Dimethylpolysiloxane | 2.0 |
| *Macadamia* nut fatty acid phytosteryl | 0.5 |
| Polyoxyethylene glyceryl isostearate | 1.0 |
| Polyoxyethylene glycerin monostearate | 1.0 |
| Sodium hexametaphosphate | 0.05 |
| PEG-12 dimethicone *³ | 1.0 |
| Spherical nylon powder | 3.0 |
| Urethane resin powder | 3.0 |

-continued

| (Component) | Blended amount (%) |
|---|---|
| Preservative | s.a. |
| Fragrance | s.a. |

The invention claimed is:

1. A water-based cosmetic characterized by comprising:
   (A) 0.1 to 5 mass % of a polyether-modified silicone having an HLB(Si) of 5 to 14;
   (B) one or more hydrophilic thickeners;
   (C) a polyol and/or ethyl alcohol; and
   (D) one or more hydrophobic powders selected from among metal oxides hydrophobically treated without using a metal soap, hydrophobic organic powders and silicone powders;
   wherein the (D) hydrophobic powder is dispersed in the water phase; and
   wherein the molecular weight of the (A) polyether-modified silicone is in the range 3,000 to 60,000.

2. The cosmetic in accordance with claim 1, wherein:
   the (B) hydrophilic thickener is at least one type selected from the group consisting of polysaccharides and derivatives thereof, and polyacrylamide compounds.

3. The cosmetic in accordance with claim 1, wherein:
   the (B) hydrophilic thickener contains a polyacrylamide compound, and further contains a polysaccharide or derivative thereof.

4. The cosmetic in accordance with claim 1, wherein:
   the hydrophobically treated metal oxide is hydrophobically treated by a silicone treatment or a fatty acid dextrin treatment.

5. The cosmetic in accordance with claim 1, wherein:
   the hydrophobic organic powder is selected from the group consisting of polymethyl methacrylate powder, nylon powder, polyurethane powder, polyethylene powder and polystyrene powder.

* * * * *